US012773189B2

(12) United States Patent
Sutton et al.

(10) Patent No.: US 12,773,189 B2
(45) Date of Patent: Oct. 27, 2026

(54) ULTRASOUND CONTROL UNIT

(71) Applicant: KONINKLIJKE PHILIPS N.V., Eindhoven (NL)

(72) Inventors: Jonathan Thomas Sutton, Boston, MA (US); Peter Bingley, Mierlo (NL); Shyam Bharat, Arlington, MA (US); Alexandra Groth, Hamburg (DE); Frank Michael Weber, Hamburg (DE); Harald Greiner, Nufringen (DE); Balasundar Iyyavu Raju, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 533 days.

(21) Appl. No.: 17/295,464

(22) PCT Filed: Nov. 15, 2019

(86) PCT No.: PCT/EP2019/081507
§ 371 (c)(1),
(2) Date: May 20, 2021

(87) PCT Pub. No.: WO2020/104330
PCT Pub. Date: May 28, 2020

(65) Prior Publication Data

US 2022/0071599 A1 Mar. 10, 2022

Related U.S. Application Data

(60) Provisional application No. 62/769,755, filed on Nov. 20, 2018.

(30) Foreign Application Priority Data

Dec. 11, 2018 (EP) .................................... 18211527

(51) Int. Cl.
*A61B 8/00* (2006.01)
*A61B 8/08* (2006.01)
*G01S 7/52* (2006.01)

(52) U.S. Cl.
CPC .......... *A61B 8/5215* (2013.01); *A61B 8/0883* (2013.01); *A61B 8/463* (2013.01); *A61B 8/54* (2013.01); *G01S 7/52053* (2013.01)

(58) Field of Classification Search
None
See application file for complete search history.

(56) References Cited

U.S. PATENT DOCUMENTS 5,997,479 A 12/1999 Savord
6,013,032 A 1/2000 Savord
(Continued)

OTHER PUBLICATIONS

International Search Report and Written Opinion of PCT/EP2019/081507, dated Mar. 2, 2020.
(Continued)

*Primary Examiner* — Michael J Carey
*Assistant Examiner* — Marjan Saboktakin

(57) ABSTRACT

An ultrasound control unit (12) is for configuring visualization of ultrasound data using in use a display unit. The control unit is adapted to acquire ultrasound image data and to automatically control visualization of the most relevant parts and views the data, based on current levels of a number of different monitored physiological parameters. In particular, responsively to one of the physiological parameters entering or leaving a pre-defined range of values (e.g. representative of an alert or normal condition respective for the patient), the control unit determines a most appropriate anatomical region within the image data for representing the changed physiological parameter, and a most useful visualization mode (e.g. view) for presenting or showing that anatomical region within the image data. One or more
(Continued)

display frames are generated which show the anatomical region visualized in accordance with the selected visualization mode. A control output is generated for controlling a display panel to display the one or more display frames.

19 Claims, 3 Drawing Sheets

(56) References Cited

U.S. PATENT DOCUMENTS

| | | | | | |
|---|---|---|---|---|---|
| 6,102,864 | A | 8/2000 | Hatfield | | |
| 6,283,919 | B1 | 9/2001 | Roundhill | | |
| 6,443,896 | B1 | 9/2002 | Detmer | | |
| 6,458,083 | B1 | 10/2002 | Jago | | |
| 6,530,885 | B1 | 3/2003 | Entrekin | | |
| 6,623,432 | B2 | 9/2003 | Powers | | |
| 6,705,992 | B2 | 3/2004 | Gatzke | | |
| 7,131,947 | B2 | 11/2006 | Demers | | |
| 9,131,882 | B2 | 9/2015 | Al-Ali | | |
| 2003/0163045 | A1 | 8/2003 | Gatzke | | |
| 2011/0201915 | A1 | 8/2011 | Gogin et al. | | |
| 2012/0083699 | A1 | 4/2012 | Reuter et al. | | |
| 2012/0116218 | A1* | 5/2012 | Martin | ................. | A61B 8/4405 600/437 |
| 2017/0215840 | A1* | 8/2017 | Gregg | .................... | A61B 5/285 |
| 2019/0090951 | A1* | 3/2019 | Camus | ................. | A61B 8/5261 |
| 2019/0343490 | A1* | 11/2019 | White | .................. | A61B 8/0883 |

OTHER PUBLICATIONS

Shalbaf, Ahmad et al, "Automatic Classification of Left Ventricular Regional Wall Motion Abnormalities in Echocardiography Images Using Nonrigid Image Registration," Journal Digital Imaging, vol. 26, No. 5, pp. 909-919, Oct. 2013.

* cited by examiner

ULTRASOUND CONTROL UNIT

CROSS-REFERENCE TO PRIOR APPLICATIONS

This application is the U.S. National Phase application under 35 U.S.C. § 371 of International Application No. PCT/EP2019/081507, filed on Nov. 15, 2019, which claims the benefit of U.S. Provisional Patent Application Ser. No. 62/769,755, filed Nov. 20, 2018 and European Patent Application No. 18211527.9, filed on Dec. 11, 2018. These applications are hereby incorporated by reference herein.

FIELD OF THE INVENTION

This invention relates to an ultrasound control unit for configuring visualization of ultrasound data.

BACKGROUND OF THE INVENTION

Ultrasound imaging is a widespread modality. One application of particular interest is the use of ultrasound for the monitoring and diagnosing of various cardiac conditions.

Recent advancements in image processing algorithms and transducer development have enabled continuous monitoring applications. Many new clinical insights can be gained from continuous monitoring as compared to a single scan. It also offers benefits over other monitoring techniques due to its non-invasiveness, absence of risk of infection, and absence of any ionizing radiation.

Ultrasound acquisition may be coupled with intelligent image analysis and signal processing algorithms for example. Such systems are becoming a valuable tool for patient monitoring at the point-of-care.

One particularly valuable application for continuous ultrasound monitoring may be cardiac hemodynamic monitoring, since it offers the potential to monitor cardiac dynamics in real time and noninvasively. It offers a viable alternative to the use of a pulmonary artery catheter, an invasive device that provides periodic measurements of cardiac output and ventricular pressure measurements. The latter is becoming increasingly unpopular with clinicians due to its invasive nature.

Monitoring enables for instance the monitoring of certain physiological or anatomical parameters, connected for instance with hemodynamics, such as cardiac output, ventricular size or volume, or other blood flow parameters.

Interpretation of ultrasound images is a more complex task than is the case for other medical image modalities. Novice ultrasound users in particular may be overwhelmed qby amount of the additional information that ultrasound can provide. In particular, the direct connection between captured ultrasound image data (e.g. of the heart) and a resulting or relevant physiological parameter (e.g. cardiac output) is defined by sophisticated image processing algorithms. This can make it very difficult for a clinician to derive additional insights from ultrasound data in a rapid manner. This can lead to the missing of critical opportunities for preventative action. This can have detrimental medical results.

A means is therefore required for intelligently processing acquired image data to extract more clinically relevant information pertaining to a current state of a patient.

SUMMARY OF THE INVENTION

The invention is defined by the claims.

According to examples in accordance with an aspect of the invention, there is provided an ultrasound control unit for configuring visualization of ultrasound data, the ultrasound control unit operably coupleable with a display unit, and the control unit comprising:

- a data acquisition module adapted to acquire ultrasound image data for a given subject from an ultrasound image data source;
- a measurement acquisition module adapted to acquire one or more physiological parameter measurements for the subject;
- a visualization module, adapted to, responsive to triggering of at least one pre-defined alert condition, defined at least by the entering or leaving of a pre-defined threshold range for at least one of the physiological parameters:
  - identify a relevant anatomical region within the acquired ultrasound image data pertaining to the at least one physiological parameter;
  - determine a visualization mode for visualizing the identified anatomical region on a display panel of the display unit, based on the at least one physiological parameter in question and on the particular alert condition triggered;
  - process at least a subset of the acquired ultrasound image data to generate one or more output display frames representative of the relevant anatomical region, and with the region visualized in accordance with the visualization mode, and generate a control output for controlling the display unit to display the one or more output display frames.

Embodiments of the invention allow more relevant image data information to be presented by identifying an anatomical region and visualization mode most relevant to a particular physiological parameter which is being monitored.

Hence embodiments of the invention essentially link up or harmonize monitored clinical measurements with ultrasound image data presentation, so that image data can be processed most appropriately for visual representation or presentation of the monitored measurement.

Moreover, display of a particular parameter is triggered specifically by a monitored physiological parameter entering or leaving a particular range of values. The entering or leaving of the range of values is representative of one or more alert conditions for the patient, thereby ensuring that the image data information visualized to the user is the most clinically relevant or urgent information at a given time.

For example, once one of the parameter variations goes beyond a predefined threshold, or leaves a normal threshold range of values, the control unit may be adapted to allocate on the display unit display panel an area, wherein a reconstructed image of an anatomical region most relevant to that parameter, given the triggered alert condition, is displayed in that area.

The pre-defined alert condition may be defined by either the entering of some threshold range of values or the leaving of a threshold range of values. For instance there may be defined an alert threshold, the entering of which indicates a dangerous level for the parameter. Additionally or alternatively, there may be defined a normal range of values, the leaving of which indicates a dangerous level for the parameter.

The ultrasound control unit may in some examples be adapted to implement a step of identifying and/or allocating a region or area of display space on a display panel of the display unit for displaying the output display frame(s). This may in some examples be based at least partly on determining or identifying a current allocation of display panel display space (to other currently visualized objects or information). The control unit may be adapted in some examples to re-assess and/or reallocate display space to currently visualized information or objects to make space for the visualization of the (new) output display frames to be displayed.

The ultrasound control unit may in some examples be adapted to cease display of a particular previously visualized and displayed output display frame once the relevant physiological parameter to which the ultrasound data displayed by the display frame corresponds moves outside of said predefined range of values. This further ensures that only the most relevant information is displayed on the display panel at any given time.

It is noted that although the data acquisition module, measurement acquisition module and visualization module are recited as separate features, their respective functionalities may be distributed in different ways among one or more components. In some examples, the functionality of the different modules may be integrated and performed by a single element, for example by a single controller or processor, or their functionalities may be otherwise distributed between one or more elements or components. Alternatively, the functionality of each module may be performed by a separate controller or processor within the ultrasound control unit.

The physiological parameter measurements may be clinical measurements. These may include for example vital signs. They may include hemodynamical measurements, in particular of the cardiac region.

The acquiring of the physiological parameter measurements may comprise deriving one or more physiological parameter measurements, for instance from the ultrasound image data, or based on signals received from other sources, such as one or more physiological parameter sensors. The measurements may be acquired from signal outputs of one or more physiological parameter sensors with which the control unit is communicatively coupleable in use.

The ultrasound image data may be acquired directly from an ultrasound imaging unit, e.g. an ultrasound transducer unit, e.g. an ultrasound probe. Alternatively, the ultrasound image data may be acquired from a different source, e.g. indirectly via a patient monitor or monitoring system, or a network to which or more ultrasound transducer units are directly coupled. The ultrasound image data may be acquired from a datastore in some examples.

The different possible visualization modes may include one or more of:

- a particular view of the relevant anatomical region within the ultrasound image data,
- an overlay of one or more physiological parameter measurements to the ultrasound image data,
- an overlay of segmentation information derived for the ultrasound image data.

A view in the present context may mean for instance a spatial view or spatial viewpoint. The visualization unit for example generates or renders an image or visual representation representing the anatomical region as (or as though) viewed from a particular viewpoint for instance.

The view may be characterized by a particular view angle or orientation, and/or a view zoom level. The view may be characterized by a (e.g. virtual) point of view location relative to the anatomical region from which the region is viewed in the rendered image.

The overlay of physiological parameter measurements may be an overlay of said measurements to an image rendered from the ultrasound image data for instance. The overlay of physiological parameter measurements may comprise any form of visual overlay representative of one or more physiological parameter measurements. The overlay may represent a distribution of one or more physiological parameter measurements across at least a portion of the identified anatomical region. The overlay may represent the one or more physiological parameter measurement in textual form in some examples, or for instance in graphical form, e.g. with colors, color gradients, or contours for instance.

Any of the above example options for the visualization mode may be combined. For example, a visualization mode may take the form of an overlay of segmentation information, e.g. with a mesh showing or describing the structure of the anatomical region, wherein the segmentation information is enhanced by representation of one or more physiological parameter measurements.

By way of one example for instance, a mesh showing the anatomical structure of at least a portion of the anatomical region might be enhanced by or combined with an overlay representing a distribution of mechanical strain across said region. For instance an overlaid structural mesh might be combined or integrated with a color gradient or contour representation of mechanical strain across the structural region (e.g. walls) represented by the mesh.

The particular view may for example include a view representative of a particular 2D plane or slice through the acquired ultrasound image data, the plane having associated plane co-ordinates and orientation angle.

The particular view may be determined for instance based on a relative orientation of the anatomical area to which the measured physiological parameter pertains. It may be based on an orientation of that region (e.g. internal walls of that region) relative to a direction of blood flow through that region.

The particular view may comprise a three dimensional representation of at least a portion of the anatomical region, optionally based on application of a mesh to the acquired ultrasound image data.

As noted above, according to one or more examples, the control unit may be adapted to generate a control output for controlling the display unit to cease display of said output display frame(s) once said pre-defined alert condition no longer holds.

According to one or more examples, the visualization module may be adapted to access a visualization database, listing for each of a plurality of different physiological parameters: at least one relevant anatomical region, and at least one relevant visualization mode for each of one or more alert conditions for the parameter. The relevant anatomical region may be identified and/or the visualization mode may be selected based on accessing the visualization database.

Alternatively, in some examples, identifying of the relevant anatomical region and/or the selecting of the visualization mode may be based on use of an algorithm for determining the anatomical region and/or visualization mode.

In some examples, the measurement acquisition module may be adapted to derive one or more of the physiological parameter measurements based on the acquired ultrasound image data. The control unit may comprise one or more algorithms or modules for processing the ultrasound image data to derive the physiological parameter measurements. In this case, the acquiring of the physiological parameter measurements comprises deriving the measurements.

By way of non-limiting example, the physiological parameter measurements may include one or more of: stroke volume, cardiac output, ejection fraction ventricular synchronicity, global or regional strain, regional wall motion.

Additionally or alternatively, the control unit may be operably coupleable with one or more physiological parameter sensors, for acquiring at least a subset of said physiological parameter measurements for the subject.

By way of non-limiting example, the physiological parameter sensors may include one or more of: an ECG sensor device, a PPG sensor, a blood pressure sensor (e.g. a blood pressure cuff).

The data acquisition module may be adapted to acquire ultrasound image data recurrently. For instance, the data acquisition module may acquire ultrasound image data continuously, or may acquire image data recurrently, for instance at regular intervals. Ultrasound image data may be acquired on an ongoing or continuing basis throughout a monitoring session for example.

The measurement acquisition unit may be adapted to continuously or recurrently acquire physiological parameter measurements for the one or more physiological parameters.

The ultrasound control unit may be adapted to continuously or recurrently monitor the acquired physiological parameter measurements. The visualization module may be adapted in use to continuously or recurrently re-evaluate which previously generated and displayed output display frames remain displayed on a display panel of the display unit.

The ultrasound control unit may be further operably coupleable with an ultrasound transducer unit, and wherein the data acquisition module is adapted to acquire the ultrasound image data using the transducer unit. For example, the control unit may be adapted to control the transducer unit acquire the data. Alternatively, a separate control element may control the acquisition, and with the control unit of the invention acquiring the data through simultaneous communication with a signal output of the transducer unit or the mentioned control element.

The control unit may in one advantageous set of embodiments be a control unit for controlling visualization of ultrasound data representative of a heart region and/or representative of a respiratory region (i.e. a region containing the lungs or a portion thereof).

In particular examples, the control unit may be for controlling visualization of cardiac ultrasound data. Here, the field of application is that of cardiac ultrasound imaging and cardiac or heart related physiological parameters, e.g. hemodynamic parameters.

The visualization module may be adapted to extract from the acquired ultrasound image data a subset of data representative of the identified anatomical region.

Examples in accordance with a further aspect of the invention provide a method of controlling visualization of ultrasound data, comprising:

- acquiring ultrasound image data for a given subject from an ultrasound image data source;
- acquiring one or more physiological parameter measurements for the subject; and
- responsive to triggering of at least one pre-defined alert condition, defined at least by the entering or leaving of a pre-defined threshold range for at least one of the physiological parameters:
  - identifying a relevant anatomical region within the acquired ultrasound image data pertaining to the at least one of the physiological parameters;
  - selecting a visualization mode for visualizing the identified anatomical region on a display panel of the display unit, based on the at least one physiological parameter in question and on the particular alert condition triggered;
  - processing at least a subset of the acquired ultrasound image data to generate one or more output display frames representative of the relevant anatomical region, and with the region visualized in accordance with the visualization mode, and generating a control output for controlling a display unit to display the output display frames.

Implementation options and details for each of the above steps may be understood and interpreted in accordance with the explanations and descriptions provided above for the apparatus aspect of the present invention (i.e. the control unit aspect).

Any of the examples, options or embodiment features or details described above in respect of the apparatus aspect of this invention (i.e. in respect of the control unit) may be applied or combined or incorporated mutatis mutandis into the present method aspect of the invention.

In particular examples, the different possible visualization modes may include one or more of:

- a particular view of the relevant anatomical region within the ultrasound image data;
- an overlay of one or more physiological parameter measurements to the ultrasound image data;
- an overlay of segmentation information derived for the ultrasound image data.

Examples in accordance with a further aspect of the invention provide an ultrasound system, comprising: an ultrasound transducer unit; and a control unit in accordance with any example or embodiment outlined above or described below, or in accordance with any claim of this application, operably coupled with the ultrasound transducer unit, and the data acquisition module of the control unit adapted to acquire the ultrasound image data using the ultrasound transducer unit.

The ultrasound transducer unit may comprise one or more ultrasonic transducers, for example one or more transducer arrays. The transducer unit may be any device or unit or element comprising at least one ultrasound transducer.

The ultrasound system may optionally further comprise a display unit, the display unit comprising a display panel, and wherein the control unit is adapted to communicate the generated control outputs to the display unit.

Where a display unit is provided, the display unit may be a display unit already comprised by the ultrasound system itself (i.e. for displaying acquired ultrasound image data while performing an examination). Alternatively, the display unit may be an additional display unit, provided in addition to the display unit already comprised by the ultrasound system.

According to one or more examples, the control unit may comprise a connection output for connecting to an external display unit in some examples. In some examples, the control unit may comprise a connection output for connecting for instance to a patient monitoring unit or system. The patient monitoring unit or system may receive the generated control outputs and use the control outputs to present a visualization of the acquired ultrasound data for instance via a display unit comprised by the patient monitoring unit or system. Alternatively, the visualization may be displayed via a separate display unit, separate for instance to any existing display unit of either the patient monitoring unit or system or the ultrasound system.

Examples in accordance with a further aspect of the invention provide a patient monitoring system, comprising:

a display unit, the display unit comprising a display panel; a patient monitoring unit; and a control unit in accordance with any example or embodiment outlined above or described below, or in accordance with any claim of this application, operably coupled with the patient monitoring unit and display unit, and adapted to communicate the generated control outputs to the display unit.

The patient monitoring unit may for example be coupleable or coupled with one or more physiological parameter (e.g. vital sign) measurement or monitoring devices. The display unit may be comprised by the patient monitoring unit, or may be a display separate to the patient monitoring unit. Where a separate display is provided, this may be in addition to a display already comprised by the patient monitoring unit or system in some examples, for instance for dedicated display of the acquired ultrasound data and the generated visualization(s).

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
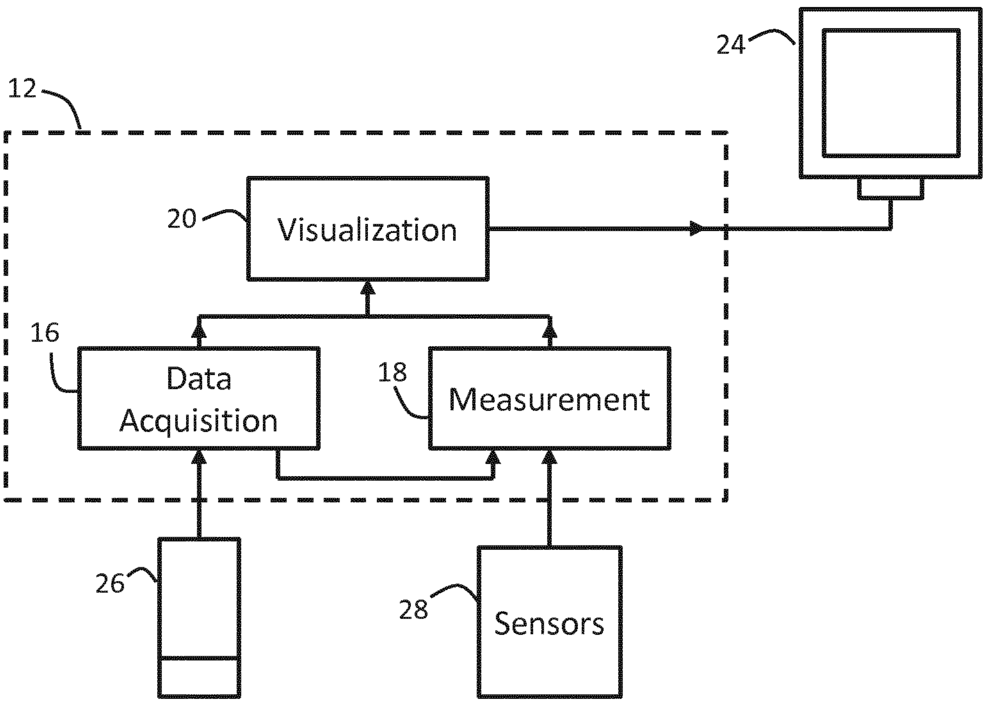
FIG. 1 shows in block diagram form an example ultrasound control unit in accordance with one or more embodiments, the control unit shown in use, operably coupled with an ultrasound transducer unit and display unit.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound control unit for configuring visualization of ultrasound data using in use a display unit. The control unit is adapted to acquire ultrasound image data and to automatically control visualization of the most relevant parts and views the data, based on current levels of a number of different monitored physiological parameters. In particular, responsive to one of the physiological parameters entering or leaving a pre-defined range of values (e.g. representative of an alert or normal condition respectively for the patient), the control unit determines a most appropriate anatomical region within the image data for representing the changed physiological parameter, and a most useful visualization mode (e.g. view) for presenting or showing that anatomical region within the image data. One or more display frames are generated which show the anatomical region visualized in accordance with the selected visualization mode. A control output is generated for controlling a display panel to display the one or more display frames.

Embodiments of the invention hence provide an aid to assist a clinician in assessing a physiological condition of a patient, and making clinical decisions. The control unit is particularly useful in continuous ultrasound monitoring applications, where it can be difficult in a short space of time to identify a most appropriate part of the gathered ultrasound data to view and the most helpful view of that part. Embodiments of the invention automatically display to a clinician a relevant portion of the ultrasound image data, in a useful visualization mode, based on up-to-date physiological measurements representative of a patient's current condition.

Hence embodiments may achieve automated triggering of specific ultrasound visualization states, these triggered for instance by changing patient physiological conditions.

An example control unit 12 in accordance with one or more embodiments of the present invention is shown in schematic block diagram form in FIG. 1. The control unit 12 is shown in use, operably coupled to an external display panel 24, an ultrasound transducer unit 26 and one or more auxiliary physiological parameter sensors 28. According to one aspect, the control unit is provided alone, and may be operably coupleable to the mentioned external units or devices. According to another aspect, the control unit may be provided in combination with one or more of the mentioned external devices: in this case, the arrangement may represent an ultrasound system. The control unit when provided by itself will be discussed now.

The ultrasound control unit 12 is for configuring visualization of ultrasound data. The control unit is operably coupleable with a display unit 24.

The ultrasound control unit 12 comprises a data acquisition module 12 adapted to acquire ultrasound image data for a given subject from an ultrasound image data source in the form (in this example) of an ultrasound transducer unit 26. The data acquisition module is operably coupleable with the ultrasound transducer unit 26 for this purpose. The transducer unit is shown so operably coupled in FIG. 1.

The ultrasound control unit further comprises a measurement acquisition module 18 adapted to acquire one or more physiological parameter measurements for the subject. The physiological parameter measurements may be acquired in different ways.

In some examples, one or more physiological parameter measurements may be derived based on the ultrasound image data acquired by the data acquisition module 16. For example, where ultrasound data of the heart is acquired, one or more hemodynamic parameters may be derivable from the image data. For ultrasound-derived measurements, the calculation of parameters may for example be based on segmentations and/or other image analysis performed on an acquired 3D volume.

Additionally or alternatively, at least a subset of the physiological parameter measurements may be acquired using one or more operably coupled physiological parameter sensors. The measurement acquisition module 18 is shown operably coupled to an arrangement of one or more auxiliary physiological parameter sensors 28. The physiological parameter sensors may include, by way of non-limiting example, one or more of: a photoplethysmography (PPG) sensor, ECG sensor device, heart rate monitor, and a blood pressure sensor.

The ultrasound control unit 12 further comprises a visualization module 20. The visualization module is adapted to perform a set of steps, for visualizing the acquired ultrasound data, responsive to the triggering of at least one pre-defined alert condition. The alert condition is defined at least by the entering or leaving of a pre-defined threshold range of at least one of the physiological parameters whose measurements are being acquired.

Ultrasound control unit 12 (e.g. the measurement acquisition module or the visualization module of the control unit) may monitor the values of the physiological parameters on a continuous or on-going basis, and detect when the level of each parameter enters or leaves a pre-defined range for that parameter.

The pre-defined alert condition may be defined by either the entering of some threshold range of values or the leaving of a threshold range of values. For instance there may be defined an alert threshold, the entering of which indicates a dangerous level for the parameter. Additionally or alternatively, there may be defined a normal range of values, the leaving of which indicates a dangerous level for the parameter.

There is preferably a pre-defined alert condition for each physiological parameter, defined at least by a pre-defined range of values for the parameter in question.

Responsive to the triggering of said at least one pre-defined alert condition, defined at least by the entering or leaving of a pre-defined threshold range of at least one of the physiological parameters whose measurements are being acquired, the visualization module 20 is adapted to first identify a relevant anatomical region within the acquired ultrasound image data pertaining to the at least one of the physiological parameters. This may be based on use of a database or lookup table listing relevant anatomical regions for each physiological parameter in some examples. This option will be described in greater detail below. In other examples, it may be based on use of an algorithm for determining an appropriate anatomical region.

Following this, the visualization module 20 is adapted to determine a visualization mode for visualizing the identified anatomical region on a display panel of the display unit, based on the at least one physiological parameter in question and on the particular alert condition triggered.

Visualization mode refers to a particular manner or mode of presenting or representing the identified anatomical region as it is captured in the ultrasound image data. It may include a particular view of the anatomical region as captured in the ultrasound image data, e.g. a particular angle or placement of a viewpoint from which the region is viewed. This may include for instance a particular cut plane through an acquired ultrasound image volume, having associated plane co-ordinates and orientation. It may include a three dimensional representation of at least a portion of the anatomical region, optionally based on rendering a mesh to the acquired ultrasound image data. Other examples of visualization modes will be discussed below.

The visualization mode is selected based on the at least one physiological parameter in question and on the particular alert condition triggered. In some examples, one visualization mode may be selected when the value falls in one range and a different mode selected when the value falls in a different range. A database or lookup table may be used in some examples for selecting the visualization mode.

Following selection of the visualization mode, the visualization module 20 is adapted to process at least a subset of the acquired ultrasound image data to generate one or more output display frames representative of the relevant anatomical region, and with the region visualized in accordance with the visualization mode.

The visualization module 20 is then adapted to generate a control output for controlling the display unit 24 to display the one or more output display frames.

Generating the display frames representative of the anatomical region may comprise extracting from the acquired ultrasound image data a subset of data representative of the identified anatomical region. This may be performed based on segmentation of the acquired ultrasound image data for instance, e.g. anatomical model-based segmentation.

It is noted that although in the above example of FIG. 1, the data acquisition module, measurement acquisition module and visualization module are shown as separate components within the ultrasound control unit 12, this is not essential. Their relevant functionalities may be distributed in different ways among one or more components. In some examples for instance, the functionality of the different modules may be integrated and performed by a single element, for example by a single controller or processor, or their functionalities may be otherwise distributed between one or more elements or components. Alternatively, the functionality of each module may be performed by a separate controller or processor within the ultrasound control unit.

Figure 2:
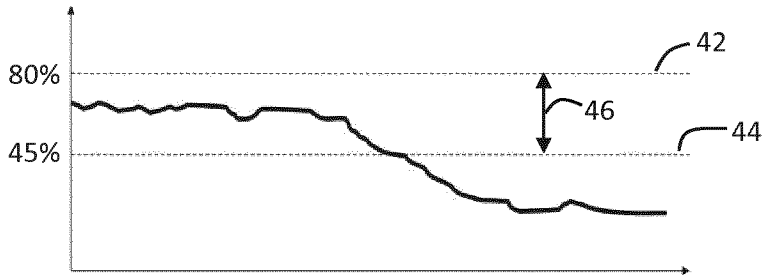
FIG. 2 illustrates triggering of an example alert condition through the leaving of an example threshold range of physiological parameter values.

One example of the procedure implemented by the control unit is illustrated in FIG. 2. The graph shows an example derived measurement signal for ejection fraction (y axis) as a function of time (x-axis), derived by the measurement acquisition module 18. Ejection fraction may be derived for instance based on acquired ultrasound image data representative of the heart, acquired by the data acquisition module 16 in an example.

Indicated in the example graph of FIG. 2 is an example pre-defined threshold range 46 of values. A pre-defined alert condition in this example is defined by the leaving of this range of values. The range 46 of values represents a normal range for ejection fraction. The pre-defined range 46 of values spans between an upper threshold boundary 42 (of 80% in this example) and a lower threshold boundary 44 (of 45% in this example). These specific numbers are exemplary only and are in no way limiting for the concept as a whole or for the physiological parameter of ejection fraction.

The ejection fraction parameter is monitored for example on a continuous basis over time. As illustrated, at a certain point in time, the parameter leaves the pre-defined normal range of values, thus triggering a pre-defined alert condition for the patient. The visualization module is in this example adapted to respond to this triggering of the alert condition by performing the set of steps for visualizing the acquired ultrasound data discussed above.

In particular, first a relevant anatomical region within the acquired ultrasound data is identified, pertaining to the parameter of ejection fraction. In this case for instance, the relevant anatomical region may be both the left and right ventricle and the mitral valve. A visualization mode is then determined for visualizing the ventricles and the mitral valve region in the best manner for illustrating the parameter of ejection fraction, and given the particular alert condition which has been triggered (i.e. low ejection fraction in this case). In this example, based for instance on consultation of a database or lookup table, or application of processing logic or an algorithm, a visualization mode may be determined corresponding (by way of example) to presenting of a 2D plane through the heart region, representing the ventricles and mitral valve, and having plane co-ordinates and angle oriented to display a two-chamber Long Axis View of this anatomical region.

The visualization module then processes the ultrasound image data to generate one or more output display frames representative of such a view of this anatomical region, and generates a control output for controlling the display unit 24 to display these one or more output display frames.

The physiological parameters acquired by the measurement acquisition module 18 may include parameters derived from ultrasound image data (and/or images or other information derived therefrom) and/or may be based on other non-ultrasound-derived physiological parameter measurements, for instance acquired using the one or more external attached sensors 28.

The ultrasound derived parameters may include by way of non-limiting example one or more cardiac related parameters, e.g. hemodynamic parameters, e.g. cardiac output, stroke volume, left ventricle volume, left ventricle pressure or any other cardiac-related parameter or other parameter. Other parameters that may be acquired include for instance mechanical strain within or across different areas of the anatomical region represented in the ultrasound image data, for instance mechanical strain across different sections of a ventricle and/or valve.

The non-ultrasound-derived physiological parameter measurements may include, by way of non-limiting example, one or more of: photoplethysmography (PPG) measurements, ECG sensor measurements, heart rate, and blood pressure.

As noted above, the visualization module 20 is adapted to determine a visualization mode for visualizing the identified anatomical region on a display panel of the display unit. The different visualization modes may correspond to different characterizing attributes of a manner in which the ultrasound image data is presented or displayed.

As noted above, a visualization mode may according to some examples correspond to a particular view of the relevant anatomical region within the ultrasound image data, where this may be a particular selected 2D plane or slice through a 3D volume captured in the ultrasound data, or may be a particular angular and/or spatial viewpoint for viewing a particular three-dimensional portion of the data corresponding to the anatomical region in question. This three-dimensional portion may be extracted or identified for visualization by means for instance of a segmentation procedure applied to the data, and adapted to permit identification of different anatomically relevant features and regions.

A visualization mode may additionally or alternatively include overlay to ultrasound image data (e.g. one or more images rendered from said data) representative of the identified anatomical region of one or more physiological parameter measurements. By this is meant overlay of textual or graphic content representative of values or levels of one or more of the acquired physiological parameter measurements.

For example, if the relevant parameter exceeding the alert threshold were cardiac output, the relevant anatomical region may be identified as the mitral valve and left ventricular apex. A view of this portion of the heart may be selected and rendered from the acquired image data, and in addition, the real-time value of the cardiac output value may be superposed atop the image(s) representing the identified heart region. The output display frame then comprises a particular view of the anatomical region and a particular physiological parameter value overlaid atop this.

Additional parameters other than the one to which the anatomical region is directly relevant may be overlaid, for additional information. For example, values of mechanical strain in or across different sections or areas of the anatomical region may be overlaid in some examples.

As noted above, the physiological parameter information may be overlaid either in textual form or a different, e.g. graphical or pictorial form. For example, mechanical strain might be represented by a polar or bulls-eye plot or other graph.

A visualization mode may additionally or alternatively include an overlay of segmentation information derived for the ultrasound image data. For example, relevant anatomical areas or features within the visualized region of the ultrasound image data may be labeled or highlighted (e.g. with block color, or with their edges highlighted).

In some examples, the visualization mode may include overlay of a derived structural mesh corresponding to the anatomical structure within the ultrasound image data. This may be derived for instance again using segmentation. For example, a ventricular contour corresponding to the outer boundary wall of the left or right ventricle may be overlaid atop a view of the relevant ventricle as represented in the ultrasound image data.

As discussed above, determination of the visualization mode for visualizing the relevant anatomical region is based at least partly on the particular alert condition which is triggered. In some examples, it may be based at least partly on the particular range of values within which the relevant parameter falls.

In some examples, the control unit may be configured to select one visualization mode in the event of a first range of the physiological parameter in question and a second, different visualization mode for a second range of the physiological parameter.

In some examples, the control unit may be adapted to continually display ultrasound image data representative of a given anatomical region. The control unit may be configured however to visualize this in accordance with a normal or standard visualization mode when the physiological parameter is within some pre-defined normal or standard range of values. The control unit may further be configured to visualize said image data in a different manner, e.g. with a different spatial viewpoint, or with certain features highlighted or enlarged, in the event that the value exceeds or falls below some pre-defined critical threshold.

In summary, the procedure performed by the visualization module is based on the determining of a customized visualization (e.g. view) of acquired ultrasound image data based on a subset of one of more of the acquired or monitored physiological parameter measurements. Selecting the particular visualization mode may be based in part on knowledge of a complete set of physiological parameters which are being acquired by the measurement acquisition unit.

The visualization steps performed by the visualization unit may encompass two parts. First: determining the particular visualization mode for visualizing the anatomical region within the ultrasound image data, e.g. the particular customization to apply to the relevant part of the ultrasound image data (e.g., choice of image plane, overlay of parameter or segmentation information, overlay of supplementary ultrasound information such as strain or color). The second part may be the means by which this visualization mode is achieved, for example the tool that is applied to perform it. The tools may include segmentation (e.g. to extract the relevant volume region of the ultrasound image data), and/or image rendering tools or processors (to render a particular view, e.g. 2D plane or 3D perspective, of the anatomical region).

By way of one example, one acquired physiological parameter may be cardiac output. If cardiac output reduces below a certain threshold, this means that the left ventricle is not pumping sufficient blood. In this case for instance, the left ventricle may be determined as the relevant anatomical region. The visualization mode might by way of example be chosen as a 2-chamber long axis view of this region, with focus on the left ventricle. To enable this, the mitral valve and left ventricular apex may be automatically segmented from the acquired 3D ultrasound volume, and the view of the anatomical region within this volume chosen as the cut plane (2D image plane) which contains these 2 features.

By way of example, Table 1 below lists a set of example physiological parameters, one or more of which may be acquired and monitored by the measurement acquisition module 18 in one or more example embodiments. For each physiological parameter is listed a corresponding pre-defined 'normal' range of values for the parameter. In this example Table therefore, the pre-defined alert condition for each physiological parameter is the leaving of the listed pre-defined normal range of values. The specific alert condition is also identified in the table for each parameter. There is also listed for each parameter a relevant anatomical region pertaining to the physiological parameter. Also listed for each parameter are one or more possible appropriate visualization modes for visualizing the identified anatomical region. These may include an appropriate 2D plane view and an appropriate 3D view.

The list presented in Table 1 is not exhaustive, and is presented for illustrative purposes only. Moreover, Table 1, by way of illustration, lists only cardiac related parameters, relevant when cardiac ultrasound imaging specifically is being performed. The inventive concept is not limited to cardiac imaging however, and when other regions of the body are being imaged, other parameters may be monitored and analyzed.

TABLE 1

| Physiological Parameter | Pre-defined Normal Range | Relevant Anatomical Region | Alert Condition | Appropriate Visualization Mode(s) |
|---|---|---|---|---|
| Cardiac Output | >2 L/min | Left Ventricle (LV) | Low Cardiac Output | Two-Chamber Long Axis View [2D plane], Cardiac Segmental Model of LV [3D mesh] |
| Ejection Fraction | >50% | Left and Right Ventricle, Valves | If low, suspect mitral regurgitation | Two-Chamber Long Axis View [2D plane], Cardiac Segmental Model of Left and/or Right Ventricle [3D mesh] Mitral Valve [3D view] |
| Ventricular Synchronicity | TsMax <80 ms | Left Ventricle, Right Ventricle | Poor contractility | Two-Chamber Long Axis View [2D plane] Cardiac Segmental Model [mesh] |
| Difference between RV and LV cardiac output | — | Left Ventricle (LV), Right Ventricle (RV) | — | Show chamber with change compared to previous scan, either LV or RV. |
| Pulmonary edema | <1 zone positive for b-lines [ACEP] | Lung, Chest | Multiple B-Line Zones Detected | Combined visualization of multiple 2D plane views of lungs |
| Global or regional tissue strain | Varies based on demographic factors | LV myocardium (measure of systolic LV function) | LV dysfunction | Long axis 2 chamber view, with overlay of strain measurements on imaged LV myocardium |
| Continuous stroke volume (SV) or stroke volume index (SVI) - derived from LV volumes (SVI = SV/Body surface area) | 81-109 mL for SV 46-58 mL/m$^2$ for SVI | Left ventricle | Low stroke volume or stroke volume index | |

TABLE 1-continued

| Physiological Parameter | Pre-defined Normal Range | Relevant Anatomical Region | Alert Condition | Appropriate Visualization Mode(s) |
|---|---|---|---|---|
| Interventricular septal shift | >'x' mm (x defined by clinical context) | Right ventricle, left ventricle | Reduced/ increased RV/LV volume | RV/LV only view |
| Mean Inferior vena cava (IVC) diameter | 1.5-2.5 cm | IVC | Shock | Bi-plane view of IVC in long and short axis |
| Regional Wall Motion | Quantitative threshold selected based on context-dependent factors. | Myocardial segment | Hypokinesis of myocardial segment | Planar view of myocardial segment demonstrating wall motion abnormality |

In the above table, Ventricular Synchronicity can refer to difference in the timing, or lack of synchrony, of contractions in different ventricles in the heart (ventricular dyssynchrony), or may refer for instance to the timing sequence of activations and contractions of different segments of the LV wall (intraventricular dyssynchrony). The example parameter TsMax in Table 1, refers to the maximal differences in time to peak myocardial systolic contraction (Ts-max) between any two of the left ventricular segments.

In Table 1, reference is made to the parameter of difference between right ventricle (RV) and left ventricle (LV) cardiac output. Here, the visualization mode May 10 depend upon which of the ventricles is showing deficiency, where this is determined based on which ventricle is exhibiting a change over time in its respective cardiac output. Whichever ventricle shows a cardiac output which is changing over time (while the other remains static for instance), the visualization mode may comprise a view of this (changing) ventricle, and may show the ventricle at two different time points, corresponding to different cardiac output values for the ventricle.

In Table 1, reference is made to Pulmonary Edema. In lung ultrasound imaging, the A-line is a horizontal artifact indicating a normal lung surface. The B-line is an artifact of a comet-tail like nature, and is indicative of subpleural interstitial edema. The more B-lines which are present in the ultrasound image of the lung, the greater the severity of this condition. By way of example, a normal range for the B-lines may be less than one lung zone showing positive indication of B-line presence.

For Interventricular septal shift referred to in Table 1 above, the normal range for the shift is typically context dependent, and may vary depending upon the patient and the clinical context. In some examples, a clinician may define the range (e.g. by inputting the normal range into the system using a user interface means) for each patient, or the normal range may be determined or computed based on clinical contextual information about the patient, such as the range of measured values of one or more other physiological parameters for the patient.

Reference is made above to a parameter of regional wall motion. The normal range for this parameter (in quantitative terms) typically depends upon patient-specific factors and is context dependent. In some examples, a normal range for the patient may be input by a clinician. By way of one example, the normal range might be set by the user based on a custom strain function, such as the integrated deviation of control points from a reference frame.

Mention has been made above of different possible views through a heart region. Reference to a long-axis view may refer for instance to the Parasternal long axis view. The long axis of the heart connects the apex and mitral valve. Reference to two chamber long axis view refers simply to the well-known apical two chamber view (which view naturally includes said long axis).

It shall be understood in the context of the present application term physiological parameters includes parameters associated with patient's health status, which are used by the medical practitioners in order to assess patient's healthcare conditions and its variation with time.

Determining the visualization mode to use may be achieved in different ways.

According to one set of examples, the visualization module may be adapted to access a visualization database, listing for each of a plurality of different physiological parameters: at least one relevant anatomical region, and at least one relevant visualization mode for each of one or more alert conditions for the parameter. The relevant anatomical region may then be identified and the visualization mode selected based on accessing the visualization database.

The database may be locally stored, for instance in a local memory, or may be stored remotely, for instance in an external data store such as an external or remote computer or server. The control unit may comprise means for communicating with said external or remote data store, for instance network communication means. This may be via an Internet link, or directly via a network link, wired or wireless, e.g. Wi-Fi.

The database may include data similar to that shown in Table 1 above for example, wherein for each of a set of physiological parameters, at least one relevant anatomical region and appropriate visualization mode are listed for each of one or more different alert conditions (defined by the entering or leaving of some defined range of values).

The database may take different forms. In some simple cases, a simple lookup table may be provided for instance. A more complex data structure for instance comprising multiple tables and/or linked fields might alternatively be used. Various different data structure means will be known and apparent to the skilled person.

In alternative examples, an algorithm may be used for determining a visualization mode to use.

In some examples, one algorithm might be used to generate or derive a physiological parameter measurement, and a separate algorithm used to derive or generate a relevant visualization mode from the full 3D image volume. Linking the result of the first algorithm to the second algorithm may be performed using a look-up table, or may alternatively be performed with a further algorithm, the further algorithm defining for instance a linear or nonlinear relationship between the two.

According to one or more examples, determining the visualization mode to apply may be based on further acquired or stored patient medical data or information. For example, a patient might in some cases have a pre-diagnosed or recognized abnormality in one anatomical region (for instance a particular region of the heart). The visualization module may according to one or more examples be adapted to consult the further source of patient information, and based on the abnormality in said given region, determine a view for visualizing the acquired ultrasound image data which encompasses or is aligned with the abnormal region. This represents just one example.

Although in above-described examples, each alert condition is defined by the entering or leaving of a range of values for a single physiological parameter, in further examples an alert condition may be defined in terms of various ranges for multiple parameters. For instance, an alert condition may only be triggered once a normal range for one parameter has been left and some defined dangerous range for a further parameter has been entered.

In one or more examples, different alert conditions may be defined in terms of different value ranges for the same physiological parameter, e.g. a warning alert range, and a critical alert range, with different visualization modes being more appropriate in each case.

In certain examples, the control unit may be adapted to generate a control output for controlling the display unit to cease display of said output display frame(s) once said pre-defined alert condition no longer holds.

The control unit may alternatively be adapted to generate a control output for controlling the display unit to alter a visualization mode of the visualized anatomical region once said at least one of the physiological parameters moves outside of said pre-defined range of values. For example a visualization mode specialized for when a patient is in a critical state may be altered once the patient leaves that critical state to change it back to a standard or normal mode of visualization.

The ultrasound control unit may in some examples be adapted to implement a step of identifying and/or allocating a region or area of display space on a display panel of the display unit for displaying the output display frame(s). This may in some examples be based at least partly on determining or identifying a current allocation of display panel display space (to other currently visualized objects or information). The control unit may be adapted in some examples to re-assess and/or reallocate display space to currently visualized information or objects to make space for the visualization of the (new) output display frames to be displayed.

The ultrasound control unit may in some examples be adapted to cease display of a particular previously visualized and displayed output display frame once the relevant physiological parameter to which the ultrasound data displayed in the display corresponds moves outside of said pre-defined range of values. This further ensures that only the most relevant information is displayed on the display panel at any given time.

According to one or more embodiments, there may be for each of a set of physiological parameters a pre-defined 'standard' or 'normal' visualization mode for visualizing ultrasound data corresponding to that parameter, when the parameter is within some normal range of values and one or more alert or abnormal visualization modes, for implementation when the parameter is not in a normal range of values (or is in an alert range of values).

The "standard" visualization mode may in some examples be user-defined (e.g. by a clinician) using a user interface means. The standard visualization mode may in some examples correspond to a particular view of ultrasound image data representative of an appropriate anatomical region. A standard view may, by way of non-limiting example, in include: a long axis 4-chamber view, a long axis 2-chamber view, a short axis view, a LV only view or any other relevant view.

As mentioned above, according to one or more embodiments, the control unit may be adapted to switch between a standard visualization mode, for visualizing ultrasound image data of a relevant anatomical region for each physiological parameter, and one or more altered or customized alert or abnormal visualization modes. The switching may be based on the triggering of relevant alert conditions for the different alert modes.

However, the original "standard" visualization mode may often still be valuable to a clinician. Therefore, according to one or more embodiments, the control unit may be adapted to implement simultaneous presentation of ultrasound data in two or more visualization modes (e.g. two or more views), where one view changes based on the ultrasound-derived measurements ("customized" visualization mode) and the other view(s) persist in accordance with the pre-defined standard view settings.

In accordance with any embodiment of the present invention, the control unit may be adapted for controlling visualization of cardiac ultrasound data. Here, the field of application is that of cardiac ultrasound imaging and cardiac or heart related physiological parameters, e.g. hemodynamic parameters.

For example, in the case that a visualization database is used for selecting the visualization mode, said visualization database may list relevant anatomical regions and/or visualization modes for at least a plurality of different cardiac-related physiological parameters. Likewise, in the case that an algorithm is used for selecting the visualization mode, the algorithm may be an algorithm adapted for deriving a relevant visualization mode for ultrasound data representative of a cardiac region.

In accordance with an advantageous set of embodiments, the data acquisition module may be adapted to continuously acquire ultrasound image data.

The measurement acquisition unit may be adapted to continuously acquire physiological parameter measurements for the one or more physiological parameters.

The ultrasound control unit 12 (for example the measurement acquisition module 18 of the control unit) may be adapted to continuously monitor the acquired physiological parameter measurements.

The visualization module 20 may be adapted to continuously update the output display frames in accordance with newly acquired ultrasound image data, to enable up-to-date imagery to be presented on the display unit 24.

The visualization module 20 may be adapted in use to continuously re-evaluate which previously generated and displayed output display frames remain displayed on a display panel of the display unit in some examples.

Figure 3:
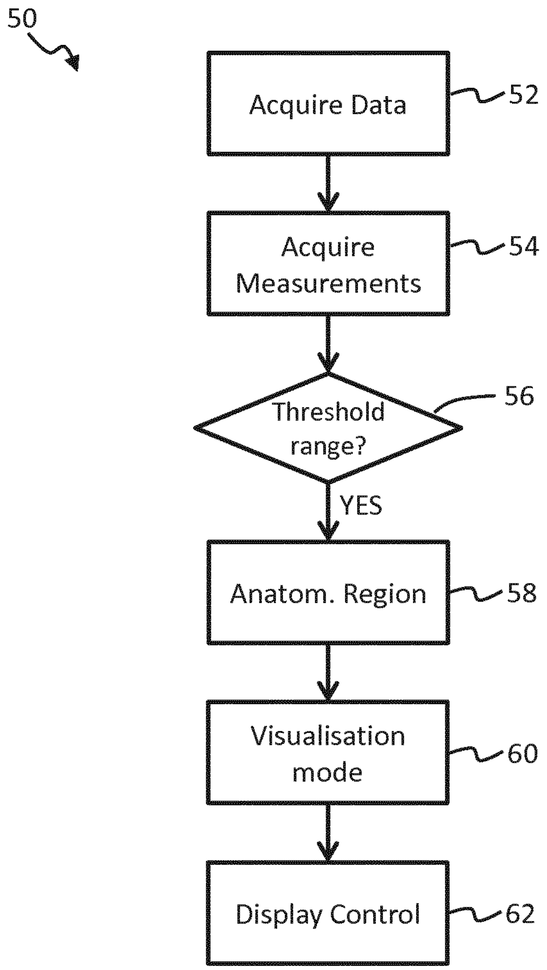
FIG. 3 shows a block diagram of an example method in accordance with one or more embodiments.

Examples in accordance with a further aspect of the invention provide a method of controlling visualization of ultrasound data. An example method 50 in accordance with one or more embodiments of this aspect of the invention is shown in block diagram form in FIG. 3.

The method 50 comprises acquiring 52 ultrasound image data for a given subject from an ultrasound image data source.

The method 50 further comprises acquiring 54 one or more physiological parameter measurements for the subject.

The method 50 further comprises: responsive to triggering 56 of at least one pre-defined alert condition, defined at least by the entering or leaving of a pre-defined threshold range for at least one of the physiological parameters:

- identifying (58) a relevant anatomical region within the acquired ultrasound image data pertaining to the at least one physiological parameter;
- selecting (60) a visualization mode for visualizing the identified anatomical region on a display panel of the display unit, based on the at least one physiological parameter in question and on the particular alert condition triggered; and
- processing (62) at least a subset of the acquired ultrasound image data to generate one or more output display frames representative of the relevant anatomical region, and with the region visualized in accordance with the visualization mode, and generating a control output for controlling a display unit to display the one or more output display frames.

Implementation options and details for each of the above steps may be understood and interpreted in accordance with the explanations and descriptions provided above in respect of the apparatus aspect of the present invention (the control unit 12 aspect).

Any of the examples, options or embodiment features or details described above in respect of the apparatus aspect of this invention (in respect of the control unit 12) may be applied or combined or incorporated mutatis mutandis into the present method aspect of the invention.

The trigger 56 of the alert condition may according to examples comprise a step of testing whether the alert condition has been met or triggered, or may comprise a continuous process of monitoring for occurrence of any of a set of pre-defined alert conditions. If no alert condition is triggered when such a testing step is performed, the testing step may in examples be repeated on a loop, or the method may in some examples loop back to the initial step 52 of acquiring ultrasound image data, and commence again from said initial step.

Examples in accordance with a further aspect of the invention provide a patient monitoring system, comprising:

- a display unit 24, the display unit comprising a display panel;
- a patient monitoring unit; and
- a control unit 12 in accordance with any example or embodiment outlined above or described below, or in accordance with any claim of this application, the control unit operably coupled with the patient monitoring unit and display unit, and adapted to communicate the generated control outputs to the display unit.

The patient monitoring unit may comprise the display unit in some examples, e.g. the display unit may be a component of the patient monitoring unit. The patient monitoring unit may comprise a controller adapted to receive signal inputs from one or more patient monitoring sensors for one or more patients and to present information corresponding to acquired signals on the display unit display panel. In other examples, the display unit may be separate to the patient monitoring unit. In some examples, the display unit may be a separate display unit, for instance provided in addition to a display unit already comprised by the patient monitoring unit or system.

The patient monitoring unit may in some examples be coupleable or coupled with one or more physiological parameter (e.g. vital sign) measurement or monitoring devices.

Figure 4:
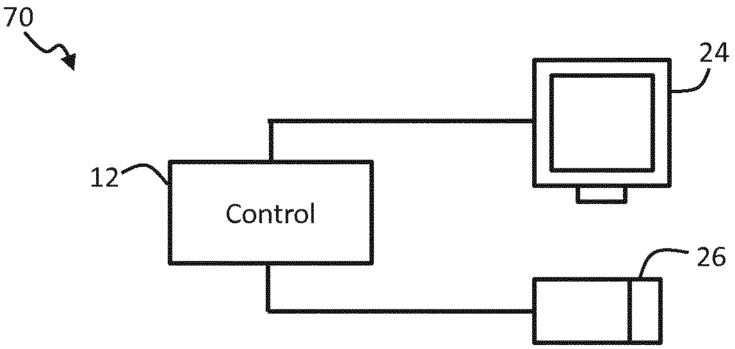
FIG. 4 shows in block diagram form an example ultrasound system in accordance with one or more embodiments.

Examples in accordance with a further aspect of the invention provide an ultrasound system. An example ultrasound system 70 in accordance with one or more embodiments of this aspect of the invention is shown in FIG. 4.

The ultrasound system 70 comprises an ultrasound transducer unit 26.

The ultrasound system 70 further comprises a control unit 12, the control unit being in accordance with any example or embodiment outlined above or described below, or in accordance with any claim of this application.

The control unit 12 is operably coupled with the ultrasound transducer unit 26.

The data acquisition module 16 (not shown) of the control unit 12 is adapted to acquire ultrasound image data by means of the ultrasound transducer unit 26.

The system in the present example further comprises a display unit 24, operably coupled with the control unit 12. The control unit is adapted to communicate each generated control output for controlling a display unit to the coupled display unit.

The ultrasound transducer unit 26 may comprise one or more ultrasonic transducers, for example one or more transducer arrays. The transducer unit may be any device or unit or element comprising at least one ultrasound transducer. The ultrasound transducer unit may comprise an ultrasound probe in examples.

Implementation options and details for each of the features of the above system may be understood and interpreted in accordance with the explanations and descriptions provided above in respect of the control unit 12 aspect of the present invention.

Any of the examples, options or embodiment features or details described above in respect of the control unit 12 may be applied or combined or incorporated mutatis mutandis into the present system aspect of the invention.

Figure 5:
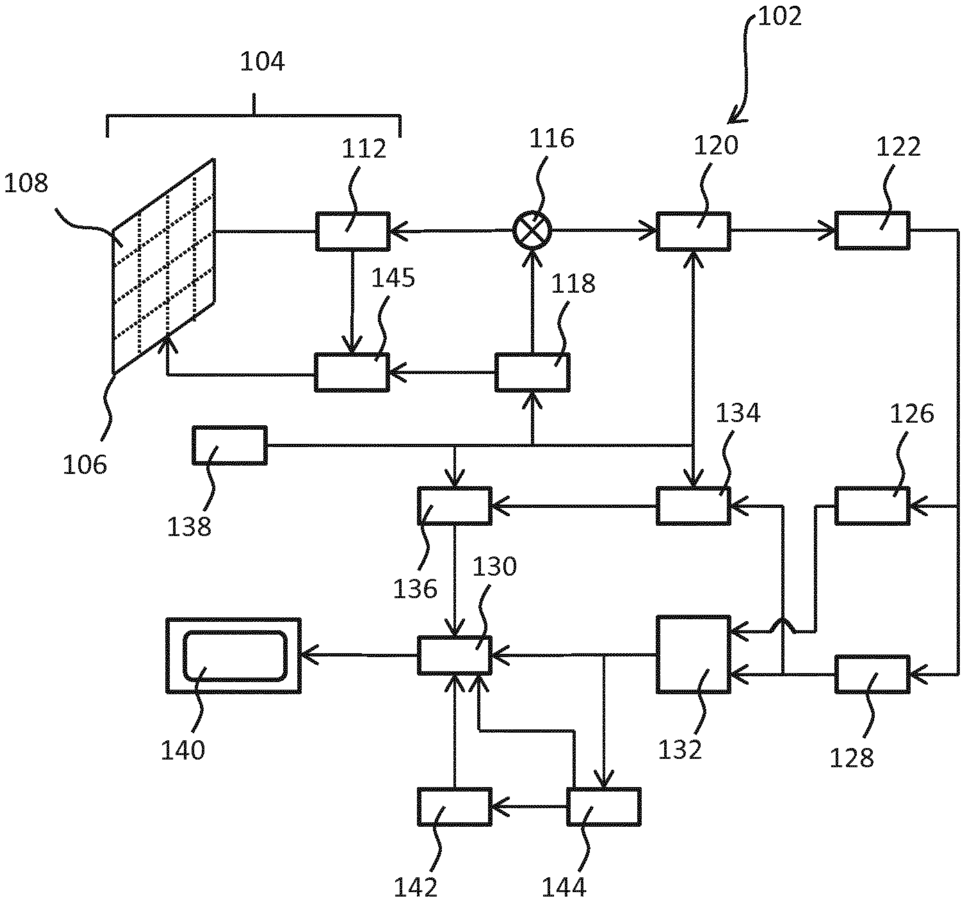
FIG. 5 shows in more detail an exemplary ultrasound system.

By way of further, more detailed explanation, a more detailed description of the general operation of an exemplary ultrasound system will now be described, with reference to FIG. 5.

The system comprises an array transducer probe 104 which has a transducer array 106 for transmitting ultrasound waves and receiving echo information. The transducer array 106 may comprise CMUT transducers; piezoelectric transducers, formed of materials such as PZT or PVDF; or any other suitable transducer technology. In this example, the transducer array 106 is a two-dimensional array of transducers 108 capable of scanning either a 2D plane or a three dimensional volume of a region of interest. In another example, the transducer array may be a 1D array.

The transducer array 106 is coupled to a microbeamformer 112 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is in general entirely optional. Further, the system includes a transmit/receive (T/R) switch 116, which the microbeamformer 112 can be coupled to and which switches the array between transmission and reception modes, and protects the main beamformer 120 from high energy transmit signals in the case where a microbeamformer is not used and the transducer array is operated directly by the main system beamformer. The transmission of ultrasound beams from the transducer array 106 is directed by a transducer controller 118 coupled to the microbeamformer by the T/R switch 116 and a main transmission beamformer (not shown), which can receive input from the user's operation of the user interface or control panel 138. The controller 118 can include transmission circuitry arranged to drive the transducer elements of the array 106 (either directly or via a microbeamformer) during the transmission mode.

The control panel 138 may be omitted, and the controller 118 directly coupled with a control unit 12 in accordance with an embodiment of the present invention, such that the controller receives input instructions from the control unit 12. In this way, the function of the control panel 138 in this example system may be facilitated by an ultrasound control unit according to an embodiment of the invention.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 118 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 118 can be coupled to control a DC bias control 145 for the transducer array. The DC bias control 145 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 112 and are then passed to a main receive beamformer 120 where the partially beamformed signals from individual patches of transducers are combined into a fully beamformed signal, referred to as radio frequency (RF) data. The beamforming performed at each stage may be carried out as described above, or may include additional functions. For example, the main beamformer 120 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 122. The signal processor 122 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 5 only the receiver beamformers 112, 120 are shown, for simplicity. In the complete system, there will also be a transmission chain with a transmission micro beamformer, and a main transmission beamformer.

The function of the micro beamformer 112 is to provide an initial combination of signals in order to decrease the number of analog signal paths. This is typically performed in the analog domain.

The final beamforming is done in the main beamformer 120 and is typically after digitization.

The transmission and reception channels use the same transducer array 106 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 126 and a Doppler processor 128. The B mode processor 126 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 128 processes temporally distinct signals arising from tissue movement and blood flow for the detection of moving substances, such as the flow of blood cells in the image field. The Doppler processor 128 typically includes a wall filter with parameters set to pass or reject echoes returned from selected types of materials in the body.

The structural and motion signals produced by the B mode and Doppler processors are coupled to a scan converter 132 and a multi-planar reformatter 144. The scan converter 132 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 140. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.).

The 2D or 3D images are coupled from the scan converter 132, multi-planar reformatter 144, and volume renderer 142 to an image processor 130 for further enhancement, buffering and temporary storage for optional display on an image display 140. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 128 and tissue structure information produced by the B mode processor 126 are coupled to a quantification processor 134. The quantification processor produces measures of different flow conditions such as the volume rate of blood flow in addition to structural measurements such as the sizes of organs and gestational age. The quantification processor may receive input from the user control panel 138, such as the point in the anatomy of an image where a measurement is to be made.

Output data from the quantification processor is coupled to a graphics processor 136 for the reproduction of measurement graphics and values with the image on the display 140, and for audio output from the display device 140. The graphics processor 136 can also generate graphic overlays for display with the ultrasound images. These graphic overlays can contain standard identifying information such as patient name, date and time of the image, imaging parameters, and the like. For these purposes the graphics processor may receive input from the user interface 138, or from a control unit 12 according to an embodiment. The user interface may also be coupled to the transmit controller 118 to control the generation of ultrasound signals from the transducer array 106 and hence the images produced by the transducer array and the ultrasound system. The transmit control function of the controller 118 is only one of the functions performed. The controller 118 also takes account of the mode of operation (for instance as directed by an operable coupled control unit 12) and the corresponding required transmitter configuration and band-pass configuration in the receiver analog to digital converter. The controller 118 can be a state machine with fixed states.

The user interface may also be coupled to the multi-planar reformatter 144 for selection and control of the planes of multiple multi-planar reformatted (MPR) images which may be used to perform quantified measures in the image field of the MPR images.

As discussed above, embodiments make use of a control unit 12. The control unit may include or may be a controller. Various other embodiments and examples discussed above make use of a controller.

A controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An ultrasound control system for configuring visualization of ultrasound data, the ultrasound control system comprising at least one processor, the ultrasound control system operably coupleable with a display, wherein the ultrasound control system is configured to:

acquire ultrasound image data for a given subject from an ultrasound image data source;

acquire one or more physiological parameter measurements for the subject;

access a visualization database, listing for each of a plurality of different physiological parameters: at least one relevant anatomical region, and at least one relevant visualization mode for each of one or more alert conditions for the one or more physiological parameter measurements; and responsive to triggering of at least one pre-defined alert condition, defined at least by the entering or leaving of a pre-defined threshold range of at least one of the one or more physiological parameter measurements:

identify the at least one relevant anatomical region within the acquired ultrasound image data pertaining to the at least one of the one or more physiological parameter measurements by accessing the visualization database;

determine the at least one relevant visualization mode for visualizing the at least one relevant anatomical region on a display panel of the display, based on the at least one of the one or more physiological parameter measurements and on the at least one pre-defined-particular alert condition triggered, by accessing the visualization database; and process a subset of the acquired ultrasound image data to generate one or more output display frames representative of the relevant anatomical region wherein the subset of the acquired ultrasound image data is extracted based on segmentation of the acquired ultrasound image data, and with the at least one relevant anatomical region visualized in accordance with the at least one relevant visualization mode, generate a control output for controlling the display to display the one or more output display frames.

2. The ultrasound control system according to claim 1, wherein the at least one relevant visualization mode includes one or more of:

a particular view of the at least one relevant anatomical region within the ultrasound image data;

an overlay of the one or more physiological parameter measurements to the ultrasound image data;

an overlay of segmentation information derived for the ultrasound image data.

3. The ultrasound control system according to claim 2, wherein said particular view includes a view representative of a particular 2D plane through the acquired ultrasound image data, the plane having associated plane co-ordinates and orientation angle.

4. The ultrasound control system according to claim 2, wherein the particular view comprises a three-dimensional representation of at least a portion of the at least one relevant anatomical region based on rendering a mesh to the acquired ultrasound image data.

5. The ultrasound control system according to claim 1, wherein the ultrasound control system is adapted to generate a control output for controlling the display to cease display of said one or more output display frames once said pre-defined alert condition no longer holds.

6. The ultrasound control system according to claim 1, wherein the ultrasound control system is configured to derive one or more of the one or more physiological parameter measurements based on the acquired ultrasound image data.

7. The ultrasound control system according to claim 1, wherein the ultrasound control system is operably coupleable with one or more physiological parameter sensors, for acquiring at least a subset of said one or more physiological parameter measurements for the subject.

8. The ultrasound control system according to claim 1, wherein the ultrasound control system is adapted to acquire ultrasound image data recurrently.

9. The ultrasound control system according to claim 1, the ultrasound control system further operably coupleable with an ultrasound transducer, and wherein the ultrasound control system is adapted to acquire the ultrasound image data using the transducer.

10. The ultrasound control system according to claim 1, wherein the ultrasound control system is for controlling visualization of ultrasound data representative of a heart region and/or representative of a respiratory region.

11. A method of controlling visualization of ultrasound data, comprising:

acquiring ultrasound image data for a given subject from an ultrasound image data source;

acquiring one or more physiological parameter measurements for the subject;

accessing a visualization database, listing for each of a plurality of different physiological parameters: at least one relevant anatomical region, and at least one relevant visualization mode for each of one or more alert conditions for the one or more physiological parameter measurements; and responsive to triggering of at least one pre-defined alert condition, defined at least by the entering or leaving of a pre-defined threshold range for at least one of the one or more physiological parameter measurements:

identifying the at least one relevant anatomical region within the acquired ultrasound image data pertaining to the at least one of the one or more physiological parameter measurements by accessing the visualization database;

selecting the at least one relevant visualization mode for visualizing the at least one relevant anatomical region on a display panel of the display unit, based on the at least one of the one or more physiological parameter measurements and on the at least one pre-defined alert condition triggered, by accessing the visualization database;

processing a subset of the acquired ultrasound image data to generate one or more output display frames representative of the at least one relevant anatomical region wherein the subset of the acquired ultrasound image data is extracted based on segmentation of the acquired ultrasound image data, and with the at least one relevant anatomical region visualized in accordance with the at least one relevant visualization mode, generating a control output for controlling a display unit to display the one or more output display frames.

12. The method as claimed in claim 11, wherein the at least one relevant visualization mode includes one or more of:

a particular view of the at least one relevant anatomical region within the ultrasound image data;

an overlay of the one or more physiological parameter measurements to the ultrasound image data, an overlay of segmentation information derived for the ultrasound image data.

13. An ultrasound imaging system, comprising:

a display;

an ultrasound transducer unit configured to acquire ultrasound image data; and at least one processor operably coupled with the ultrasound transducer unit, wherein the at least one processor is configured to:

acquire a set of physiological parameter measurements based on the ultrasound image data;

identify an occurrence of an alert condition associated with a physiological parameter measurement of the set of physiological parameter measurements, wherein the alert condition is identified based on comparing the physiological parameter measurement to a threshold range;

access a visualization database, listing for each of a plurality of different physiological parameters: at least one relevant anatomical region, and at least one relevant visualization mode for each of one or more alert conditions for-associated with each physiological parameter measurement of the set of physiological parameter measurements; and determine, based on the physiological parameter measurement, the at least one relevant anatomical region in the ultrasound image data by accessing the visualization database; and cause display, on the display, of display frames representative of the at least one relevant anatomical region by processing a subset of the acquired ultrasound image data wherein the subset of the acquired ultrasound image data is extracted based on segmentation of the acquired ultrasound image data and wherein causing display of the display frames representative of the at least one relevant anatomical region includes determining the at least one relevant visualization mode for displaying the at least one relevant anatomical region based on the alert condition and the at least one relevant anatomical region by accessing the visualization database.

14. A patient monitoring system, comprising:

a display unit, the display unit comprising a display panel;

a patient monitoring unit; and an ultrasound control system according to claim 1, operably coupled with the patient monitoring unit and display unit, and adapted to communicate the generated control output to the display unit.

15. The ultrasound control system of claim 1, further configured to:

allocate display space on the display for the one or more output display frames.

16. The ultrasound control system of claim 15, wherein allocating the display space includes identifying a current allocation of the display space for currently displayed data and modifying the current allocation of the display space for display of the one or more output display frames.

17. The ultrasound imaging system of claim 14, wherein the at least one relevant anatomical region is displayed according to a first visualization mode when the physiological parameter is within the threshold range and according to a second visualization mode different from the first visualization mode when the physiological parameter is outside the threshold range.

18. The ultrasound imaging system of claim 14, wherein determining the at least one relevant visualization mode includes determining an ultrasound imaging mode or operation to achieve the at least one relevant visualization mode.

19. The ultrasound imaging system of claim 14, wherein the at least one relevant visualization mode is determined based, at least in part, on a known patient condition.

* * * * *